US009786110B2

(12) United States Patent
Yamamoto et al.

(10) Patent No.: US 9,786,110 B2
(45) Date of Patent: Oct. 10, 2017

(54) ON-VEHICLE APPARATUS CONTROL SYSTEM AND ON-VEHICLE CONTROL DEVICE

(71) Applicants: Masahiro Yamamoto, Aichi (JP); Yoichi Atsumi, Aichi (JP)

(72) Inventors: Masahiro Yamamoto, Aichi (JP); Yoichi Atsumi, Aichi (JP)

(73) Assignee: OMRON AUTOMOTIVE ELECTRONICS CO., LTD., Aichi (JP)

( * ) Notice: Subject to any disclaimer, the term of this patent is extended or adjusted under 35 U.S.C. 154(b) by 0 days.

(21) Appl. No.: 15/200,043

(22) Filed: Jul. 1, 2016

(65) Prior Publication Data

US 2017/0004664 A1 Jan. 5, 2017

(30) Foreign Application Priority Data

Jul. 3, 2015 (JP) ................................ 2015-134453

(51) Int. Cl.
*C07C 9/00* (2006.01)
*G07C 9/00* (2006.01)

(52) U.S. Cl.
CPC .................... *G07C 9/00309* (2013.01); *G07C 2009/00555* (2013.01)

(58) Field of Classification Search
CPC ..... B60R 25/04; B60R 25/24; G07C 9/00309; G07C 2209/63; G07C 2009/00793
See application file for complete search history.

(56) References Cited

U.S. PATENT DOCUMENTS 6,816,081 B1 * 11/2004 Okada ................ G07C 9/00182 340/12.5
2006/0261925 A1 * 11/2006 Baumgartner .......... B60R 25/04 340/5.62
2007/0024416 A1 * 2/2007 Tang ..................... B60R 25/245 340/5.61

FOREIGN PATENT DOCUMENTS

JP 2008-127777 A 6/2008
JP 2012-051421 A 3/2012

OTHER PUBLICATIONS

Machine Translation of JP 2008-127777A.*

* cited by examiner

*Primary Examiner* — Nabil Syed
(74) *Attorney, Agent, or Firm* — Osha Liang LLP

(57) ABSTRACT

An on-vehicle control device mounted on a vehicle includes: an on-vehicle transmission unit that transmits a response request signal to a portable machine carried by a user; and an on-vehicle reception unit that receives a response signal transmitted from the portable machine in response to reception of the response request signal, and a remote control signal transmitted from the portable machine in response to an operation on an operation switch disposed in the portable machine. The on-vehicle reception unit performs: reception processing on the remote control signal on a basis of a first reception sensitivity when receiving the remote control signal transmitted from the portable machine; and reception processing on the response signal on a basis of a second reception sensitivity lower than the first reception sensitivity when receiving the response signal transmitted from the portable machine.

8 Claims, 10 Drawing Sheets

<KEYLESS ENTRY>

ON-VEHICLE APPARATUS CONTROL SYSTEM AND ON-VEHICLE CONTROL DEVICE

CROSS-REFERENCES TO RELATED APPLICATIONS

This application is based upon and claims the benefit of priority from Japanese Patent Application No. 2015-134453, filed on Jul. 3, 2015; the entire contents of which are incorporated herein by reference.

FIELD

One or more embodiments of the present invention relate to an on-vehicle apparatus control system in which an on-vehicle apparatus is controlled on the basis of radio signals which are transmitted and received between an on-vehicle control device mounted on a vehicle and a portable machine carried by a user, and, particularly to a crime prevention technique for the vehicle.

BACKGROUND

There is an on-vehicle apparatus control system in which control of an on-vehicle apparatus is performed, such as locking and unlocking of a door, and starting of an engine, on the basis of radio signals which are transmitted and received between an on-vehicle control device mounted on a vehicle and a portable machine carried by a user. Communication methods between the on-vehicle control device and the portable machine are roughly classified into three methods such as a polling method, a passive entry method, and a keyless entry method.

In the polling method, the on-vehicle control device transmits a response request signal at a predetermined cycle regardless of a position of the portable machine. If the response request signal is received, the portable machine returns a response signal to the on-vehicle control device. In the passive entry method, when a user comes close to or comes into contact with a door knob, a passive request switch is turned on, and the on-vehicle control device transmits a response request signal to the portable machine. If the response request signal is received, the portable machine returns a response signal to the on-vehicle control device. In the keyless entry method, a response request signal is not transmitted from the on-vehicle control device to the portable machine, and, when the user operates the portable machine, a remote control signal is transmitted to the on-vehicle control device from the portable machine. In any case, if the response signal or the remote control signal is received from the portable machine, the on-vehicle control device performs collation between ID codes included in the signal. If the collation is successful, the on-vehicle control device locks or unlocks a door of the vehicle, or starts an engine thereof.

The portable machine operates with power of a battery built thereinto. In order to increase a service life of the battery of the portable machine, for example, in JP-A-2008-127777, a transmission output level of a signal from a portable machine is switched during passive entry and during keyless entry. Specifically, during keyless entry in which an operation switch of the portable machine is operated, a remote control signal is transmitted in a first transmission output level from the portable machine. During passive entry in which a passive request switch is operated, a response signal is transmitted in a second transmission output level lower than the first transmission output level from the portable machine. In a case where the response signal transmitted from the portable machine cannot be received by an on-vehicle apparatus, a response signal is transmitted again in the first transmission output level from the portable machine.

Meanwhile, in a case of the polling method or the passive entry method, for example, an illegal communication act may be performed in which the portable machine which is far away disguises itself as being in close proximity to a vehicle as a result of a relay relaying a response request signal transmitted from the on-vehicle control device and the portable machine receiving the response request signal. The illegal communication act using the relay is called relay attack. A malicious third party who is not an owner of a vehicle may commit a crime such as theft of the vehicle by unlocking a door of the vehicle or starting an engine through the relay attack.

Therefore, regarding crime prevention countermeasures against the relay attack, for example, in JP-A-2012-051421, an attenuation rate of a signal transmitted from a portable machine is switched during passive entry and during keyless entry. Specifically, during keyless entry in which an unlock switch of the portable machine is operated, an RF transmission unit of the portable machine attenuates a door unlocking signal to a low attenuation rate, and transmits the door unlocking signal to an on-vehicle apparatus. During passive entry in which a passive request switch (touch sensor) is operated, the RF transmission unit of the portable machine attenuates a response signal (an identification signal including an ID code) to a high attenuation rate, and transmits the response signal to the on-vehicle apparatus.

If an output level of a signal transmitted from the portable machine is simply reduced, or an attenuation rate is merely increased as relay attack countermeasures, the relay attack can be suppressed, but there is a concern that the transmitted signal (electric wave) may be canceled out by external noise, and thus may not be received normally by the on-vehicle control device.

In a case where an output level or an attenuation rate of a signal transmitted from the portable machine is switched as relay attack countermeasures, a circuit for the changing is required to be provided in the portable machine. However, in a case where such a circuit is provided, a circuit configuration or signal processing becomes complex, and this is contrary to demands for miniaturization of the portable machine.

SUMMARY

One or more embodiments of the present invention improves crime prevention performance against a relay attack without making a portable machine complex while securing a communication function between an on-vehicle control device and the portable machine.

In accordance with one aspect of the present invention, an on-vehicle apparatus control system includes: an on-vehicle control device mounted on a vehicle; and a portable machine carried by a user. The on-vehicle control device includes: an on-vehicle transmission unit that transmits a response request signal to the portable machine; and an on-vehicle reception unit that receives a response signal and a remote control signal from the portable machine. The portable machine includes: a portable machine reception unit that receives the response request signal from the on-vehicle control device; an operation switch with which an on-vehicle apparatus mounted on the vehicle is operated; and a portable machine transmission unit that transmits the response signal in response to reception of the response request signal, and transmits the remote control signal in response to an operation on the operation switch. The on-vehicle control device controls the on-vehicle apparatus on a basis of the response signal or the remote control signal received by the ort-vehicle apparatus reception unit. The on-vehicle reception unit performs: reception processing on the remote control signal on a basis of a first reception sensitivity when receiving the remote control signal transmitted from the portable machine transmission unit; and reception processing on the response signal on a basis of a second reception sensitivity lower than the first reception sensitivity when receiving the response signal transmitted from the portable machine transmission unit.

According to the aspect, when the remote control signal is received, the on-vehicle reception unit performs reception processing on the remote control signal transmitted from the portable machine on the basis of the first reception sensitivity higher than the second reception sensitivity. Therefore, in a case where the portable machine is located within an arrival distance of the remote control signal even if the portable machine is not located in the vicinity of the vehicle, the remote control signal can be reliably received, and thus the on-vehicle apparatus can be operated. When the response signal for the response request signal is received, the on-vehicle reception unit performs reception processing on the response signal transmitted from the portable machine on the basis of the second reception sensitivity lower than the first reception sensitivity. Therefore, if the portable machine is located in the vicinity of the vehicle, the response signal can be reliably received, and thus the on-vehicle apparatus can be controlled. In a case where a relay attack using relays is performed, if the portable machine is located at a position separated from the vehicle, the signal intensity of the response signal transmitted from the portable machine is low so that the response signal is not received by the on-vehicle reception unit on the basis of the second reception sensitivity, and thus the relay attack can be stopped. Since the on-vehicle control device side only has to switch the sensitivity for receiving a signal, a circuit configuration of or signal processing in the portable machine side is not complex. Therefore, it is possible to improve the crime prevention performance against a relay attack without making the portable machine complex while securing a communication function between the on-vehicle control device and the portable machine.

In one or more embodiments of the present invention, the on-vehicle transmission unit may transmit the response request signal when an on-vehicle switch disposed in the vehicle is operated, or intermittently at a predetermined cycle.

In one or more embodiments of the present invention, the on-vehicle reception unit may include: an on-vehicle reception antenna via which an external signal is received; and an attenuator that attenuates a signal received via the on-vehicle reception antenna, and the on-vehicle reception unit may perform: in the first reception sensitivity, a process of detecting the remote control signal from a signal received via the on-vehicle reception antenna; and in the second reception sensitivity, a process of attenuating a signal received via the on-vehicle reception antenna with the attenuator, and detecting the response signal from an attenuated signal.

In one or more embodiments of the present invention, the on-vehicle reception unit may include: an on-vehicle reception antenna via which an external signal is received; and a signal intensity measurement portion that measures the intensity of a signal received via the on-vehicle reception antenna, and the on-vehicle reception unit may perform: in the first reception sensitivity, a process of detecting the remote control signal from a signal received via the on-vehicle reception antenna; and in the second reception sensitivity, process of measuring the intensity of a signal received via the on-vehicle reception antenna with the signal intensity measurement portion, and detecting the response signal from the signal received via the on-vehicle reception antenna only in a case where a measured value is equal to or greater than a threshold value.

According to one or more embodiments of the present invention, it is possible to improve crime prevention performance against a relay attack without making a portable machine complex while securing a communication function between an on-vehicle control device and the portable machine.

DETAILED DESCRIPTION

Figure 1:
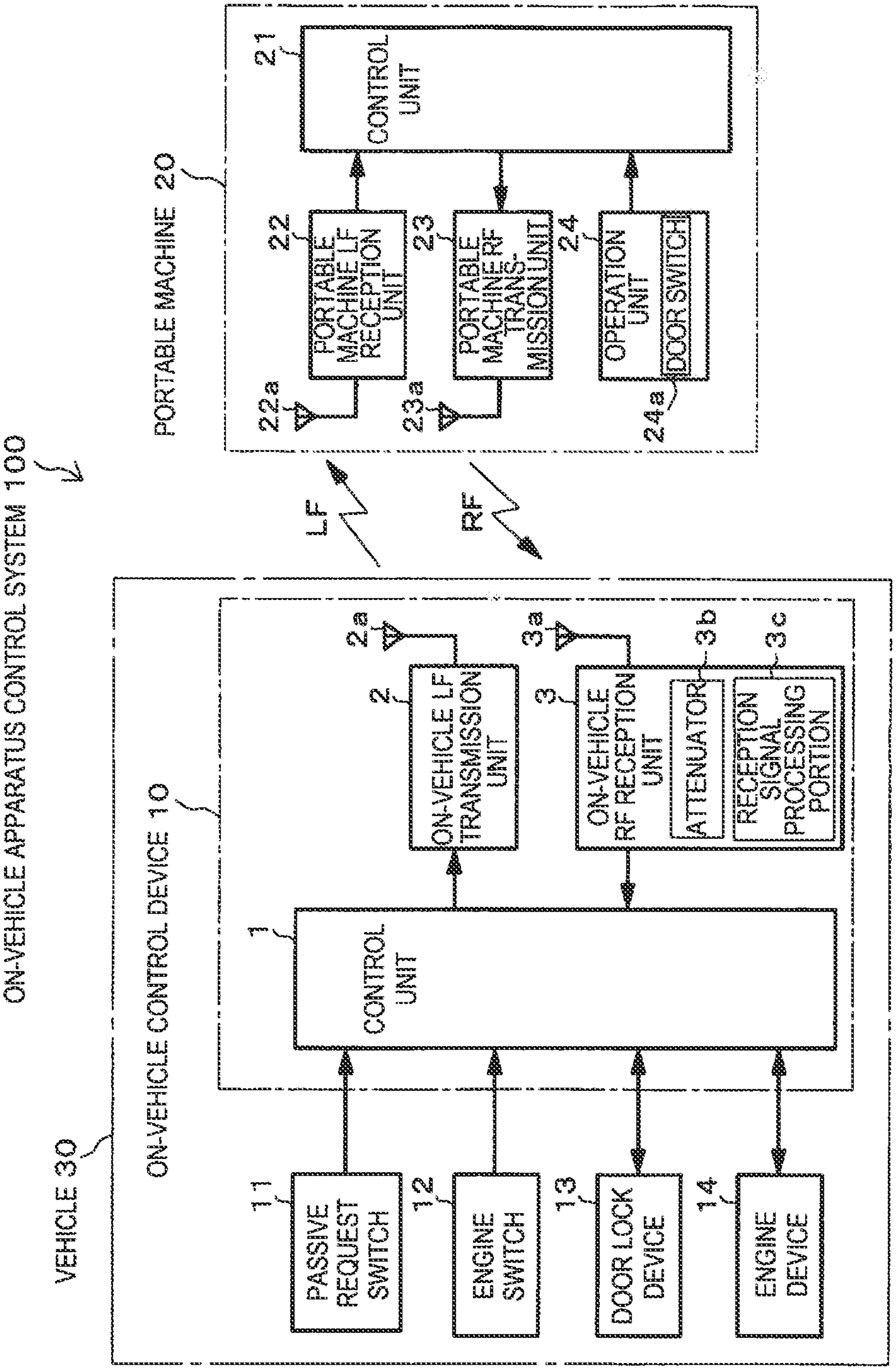
FIG. 1 is a configuration diagram of an on-vehicle apparatus control system according to a first embodiment of the present invention.

In embodiments of the invention, numerous specific details are set forth in order to provide a thorough understanding of the invention. However, it will be apparent to one of ordinary skill in the art that the invention may be practiced without these specific details. In other instances, well-known features have not been described in detail to avoid obscuring the invention.

Hereinafter, embodiments of the present invention will be described with reference to the drawings. The same portions or corresponding portions are given the same reference numerals throughout the drawings.

First, with reference to FIG. 1, a description will be made of a configuration of an on-vehicle apparatus control system 100 according to a first embodiment.

FIG. 1 is a diagram illustrating a configuration of the on-vehicle apparatus control system 100 according to the first embodiment. The on-vehicle apparatus control system 100 includes an on-vehicle control device 10 and a portable machine 20. In the on-vehicle apparatus control system 100, control on an on-vehicle apparatus mounted on a vehicle 30 is performed on the basis of radio signals which are transmitted and received between the on-vehicle control device 10 and the portable machine 20.

In the present embodiment, the control on an on-vehicle apparatus indicates control on a door lock device 13 which locks or unlocks a door of the vehicle 30 constituted of an automatic four-wheel vehicle. The vehicle 30 is provided with a plurality of doors which can be locked and unlocked.

The on-vehicle control device 10, a passive request switch 11, an engine switch 12, the door lock device 13, and an engine device 14 are mounted on the vehicle 30. The portable machine 20 is carried by a user of the vehicle 30.

The on-vehicle control device 10 includes a control unit 1, an on-vehicle low frequency (LF) transmission unit 2, and an on-vehicle radio frequency (RF) reception unit 3. The control unit 1 is constituted of a CPU, a memory, and the like.

The on-vehicle LF transmission unit 2 is constituted of an on-vehicle transmission antenna 2*a*, a transmission signal processing portion (not illustrated), and the like. The on-vehicle LF transmission unit 2 transmits an LF signal generated by the transmission signal processing portion to the portable machine 20 via the on-vehicle transmission antenna 2*a*.

A plurality of on-vehicle LF transmission units 2 are provided to be distributed inside and outside a vehicle interior of the vehicle 30. Thus, LF signals transmitted from the on-vehicle LF transmission units 2 spread to the vicinity (outside of the vehicle interior) of the vehicle 30 and to the inside of the vehicle interior. The LF signal transmitted by the on-vehicle LF transmission unit 2 includes a response request signal for the portable machine 20. The on-vehicle LF transmission unit 2 is an example of an "on-vehicle transmission unit" according to one or more embodiments of the present invention.

The on-vehicle RF reception unit 3 is constituted of an on-vehicle reception antenna 3*a*, an attenuator 3*b*, a reception signal processing portion 3*c*, and the like. The ort-vehicle reception antenna 3*a* receives a signal from the outside. The attenuator 3*b* attenuates a signal received via the on-vehicle reception antenna 3*a*. The reception signal processing portion 3*c* performs a process of detecting a predetermined RF signal from the signal received via the on-vehicle reception antenna 3*a*.

The on-vehicle RF reception unit 3 drives the respective portions 3*a* to 3*c* so as to receive RF signals transmitted from the portable machine 20. The RF signals received by the on-vehicle RF reception unit 3 include a response signal and a remote control signal transmitted from the portable machine 20. The on-vehicle RF reception unit 3 is an example of an "on-vehicle reception unit" according to one or more embodiments of the present invention.

The control unit 1 controls the on-vehicle LF transmission unit 2 and the on-vehicle RF reception unit 3 so as to perform wireless communication with the portable machine 20, and to transmit and receive signals or information to and from the portable machine 20. The control unit 1 switches a sensitivity with which the on-vehicle RF reception unit 3 receives a signal, to a first reception sensitivity or a second reception sensitivity lower than the first reception sensitivity.

Specifically, if the control unit 1 switches the sensitivity of the on-vehicle RF reception unit 3 to the first reception sensitivity, a signal received via the on-vehicle reception antenna 3*a* is input to the reception signal processing portion 3*c* without using the attenuator 3*b*, and a predetermined RF signal is detected by the reception signal processing portion 3*c*. In other words, the RF signal transmitted from the portable machine 20 undergoes reception processing on the basis of the first reception sensitivity.

If the control unit 1 switches the sensitivity of the on-vehicle RF reception unit 3 to the second reception sensitivity, a signal received via the on-vehicle reception antenna 3*a* is attenuated by the attenuator 3*b* so as to be then input to the reception signal processing portion 3*c*, and a predetermined RF signal is detected by the reception signal processing portion 3*c*. In other words, the RF signal transmitted from the portable machine 20 undergoes reception processing on the basis of the second reception sensitivity. In this case, if a signal received via the on-vehicle reception antenna 3*a* is a signal with low intensity which almost disappears due to attenuation in the attenuator 3*h*, a predetermined RF signal is not detected by the reception signal processing portion 3*c*.

If a response signal or a remote control signal is received as the predetermined RF signal by the on-vehicle RF reception unit 3, the control unit 1 collates an ID code (identification information) of the portable machine 20 included in the signal with an ID code of the on-vehicle control device 10 stored in advance.

The passive request switch 11, the engine switch 12, the door lock device 13, and the engine device 14 are connected to the on-vehicle control device 10.

The passive request switch 11 is provided on a door knob disposed on an outer surface of a body of the vehicle 30, and is operated in order to lock and unlock the door of the vehicle 30. The passive request switch 11 is an example of an "on-vehicle switch" according to one or more embodiments of the present invention. The engine switch 12 is provided around a driver's seat in the vehicle interior of the vehicle 30, and is operated in order to start and stop the engine.

If the user operates the passive request switch 11 or the engine switch 12, an operation signal corresponding, to the operation is transmitted to the control unit 1 of the on-vehicle control device 10.

The door lock device 13 is constituted of a mechanism locking and unlocking each door of the vehicle 30, and a driving circuit of the mechanism. The engine device 14 is constituted of a starter motor starting the engine of the vehicle 30, a driving circuit of the starter motor, and the like. The door lock device 13 is an example of an "on-vehicle apparatus" according to one or more embodiments of the present invention.

The portable machine 20 is constituted of an FOB key. The portable machine 20 includes a control unit 21, a portable machine LF reception unit 22, a portable machine RF transmission unit 23, and an operation unit 24. The control unit 21 is constituted of a CPU, a memory, and the like.

The portable machine LF reception unit 22 is constituted of a portable machine reception antenna 22*a* and a reception signal processing portion (not illustrated). The portable machine LF reception unit 22 receives an LF signal transmitted from the on-vehicle control device 10 via the portable machine reception antenna 22*a*. The LF signal received by the portable machine LF reception unit 22 includes the above-described response request signal. The portable machine LF reception unit 22 is an example of a "portable machine reception unit" according to one or more embodiments of the present invention.

The portable machine RF transmission unit 23 is constituted of a portable machine transmission antenna 23*a*, a transmission signal processing portion (not illustrated), and the like. The portable machine RF transmission unit 23 transmits an RF signal generated by the transmission signal processing portion to the on-vehicle control device 10 via the portable machine transmission antenna 23*a*. The RF signal transmitted by the portable machine RF transmission unit 23 includes the above-described response signal. The portable machine RF transmission unit 23 is an example of a "portable machine transmission unit" according to one or more embodiments of the present invention.

The control unit 21 controls the portable machine LF reception unit 22 and the portable machine RF transmission unit 23 so as to perform wireless communication with the on-vehicle control device 10, and to transmit and receive signals or information to and from the on-vehicle control device 10.

The operation unit 24 is provided with a door switch 24*a*. The door switch 24*a* is operated in order to lock and unlock the door of the vehicle 30.

If the user operates the door switch 24*a*, the control unit 21 generates a remote control signal corresponding to the operation, and transmits the remote control signal to the on-vehicle control device 10 from the portable machine RF transmission unit 23. In other words, the RF signal transmitted by the portable machine RF transmission unit 23 also includes the remote control signal. If the remote control signal is received by the on-vehicle RF reception unit 3, the control unit 1 of the on-vehicle control device 10 collates an ID code of the portable machine 20 included in the remote control signal with the ID code of the on-vehicle control device 10 stored in advance. In a case where the collation between the ID codes is successful (both of the ID codes match each other), the control unit 1 controls the door lock device 13 to lock or unlock each door of the vehicle 30 (keyless entry method).

If the user carrying the portable machine 20 comes close to the vehicle 30, and operates the passive request switch 11, the control unit 1 of the on-vehicle control device 10 transmits a response request signal to the portable machine 20 from the on-vehicle LF transmission unit 2. If the response request signal is received by the portable machine LF reception unit 22, the control unit 21 of the portable machine 20 generates a response signal, and transmits the response signal to the on-vehicle control device 10 from the portable machine RF transmission unit 23. If the response signal is received by the on-vehicle RF reception unit 3, the control unit 1 of the on-vehicle control device 10 collates an ID code of the portable machine 20 included in the response signal with the ID code of the on-vehicle control device 10 stored in advance. In a case where the collation between the ID codes is successful, the control unit 1 controls the door lock device 13 on the basis of the response signal to lock or unlock each door of the vehicle 30 (passive entry method).

If the user carrying the portable machine 20 operates the engine switch 12 in the vehicle interior of the vehicle 30, the control unit 1 performs communication with the portable machine LF reception unit 22 and the portable machine RF transmission unit 23 of the portable machine 20 by using the on-vehicle LF transmission unit 2 and the on-vehicle RF reception unit 3, and collates the ID code of the on-vehicle control device 10 and the ID code of the portable machine 20. If the collation between the ID codes is successful, the control unit 1 controls the engine device 14 to start or stop the engine of the vehicle 30.

However, relays 51 and 52 (refer to FIG. 7 which will be described later) used for a relay attack have a function of relaying transmission and reception of a signal between the on-vehicle control device 10 and the portable machine 20, even if the portable machine 20 is far away from the vehicle 30. As a result, the portable machine 20 which is far away is disguised as if it were located near the vehicle 30, and thus illegal communication is performed.

Next, operations of the on-vehicle control device 10 and the portable machine 20 according to the first embodiment will be described with reference to FIGS. 2 to 7.

In this example, it is assumed that the portable machine 20 is located outside the vehicle interior of the vehicle 30, and the engine of the vehicle 30 is stopped (this is also the same for other embodiments which will be described later).

Figure 2:
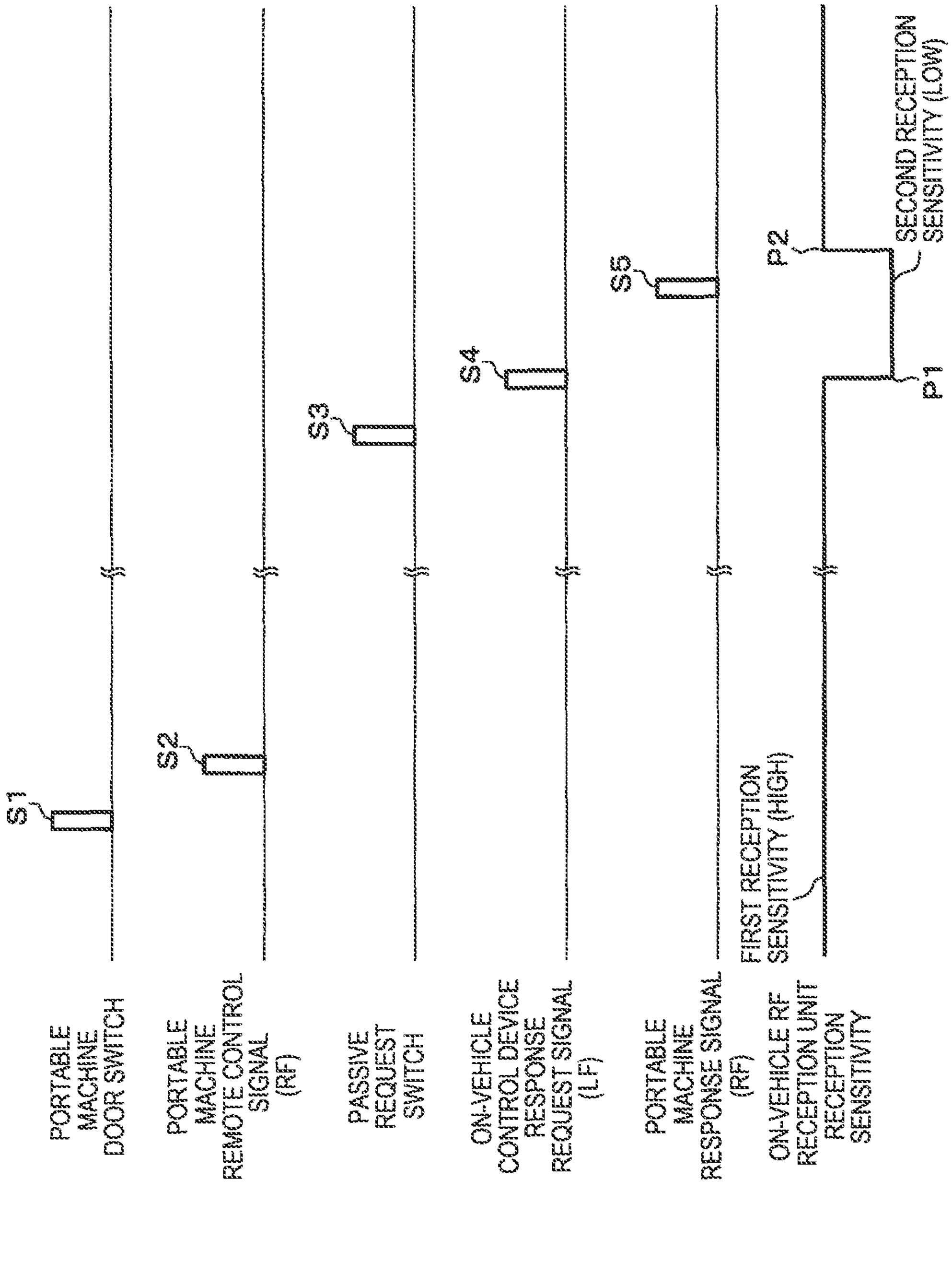
FIG. 2 is a diagram illustrating signals transmitted and received between an on-vehicle control device and a portable machine illustrated in FIG. 1, and a switching state of reception sensitivity of an RF reception unit.
Figure 3:
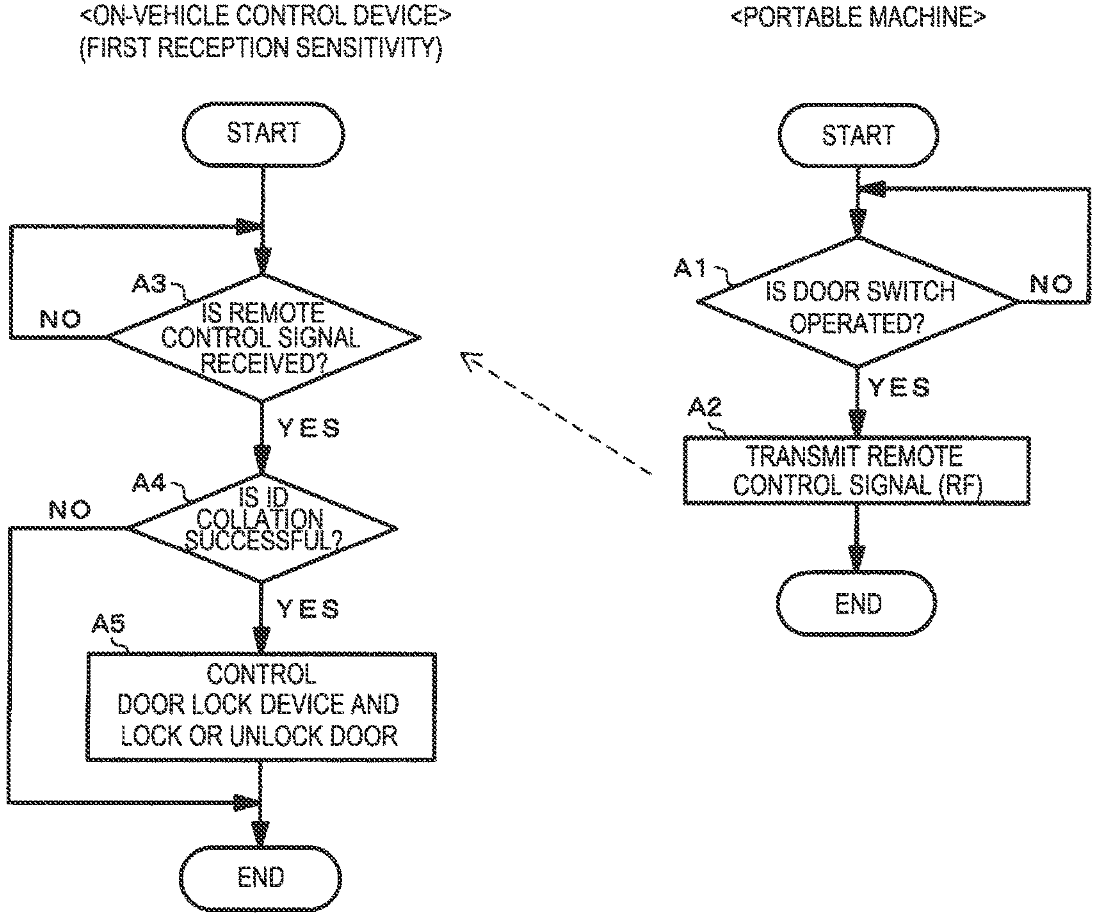
FIG. 3 is a flowchart illustrating operations of the on-vehicle control device and the portable machine illustrated in FIG. 1 during keyless entry.
Figure 5:
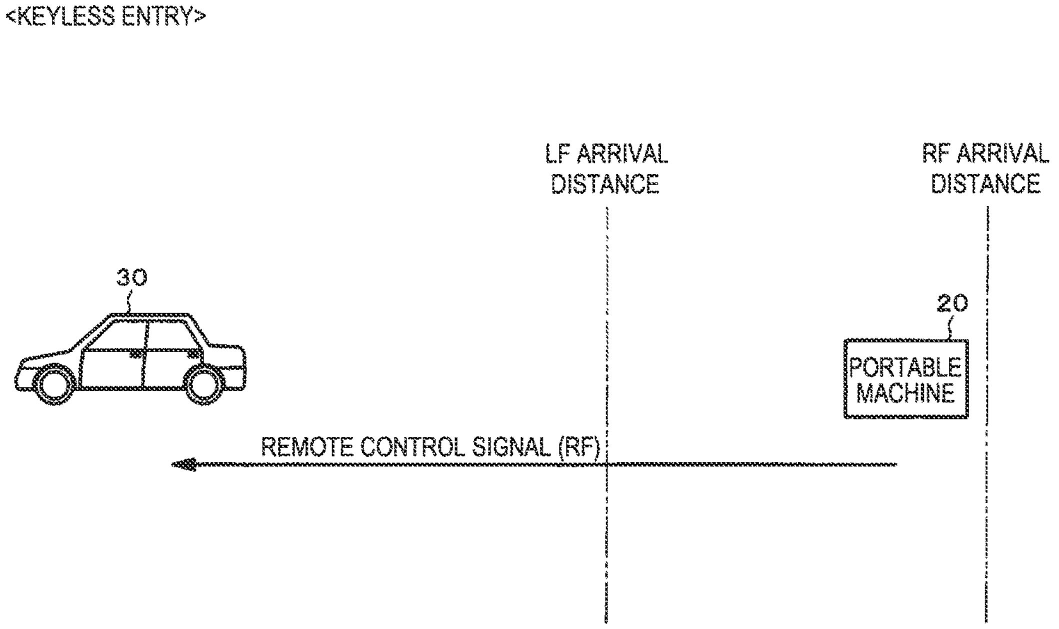
FIG. 5 is a diagram illustrating examples of positions of the on-vehicle control device and the portable machine illustrated in FIG. 1 and a communication state therebetween during keyless entry.

FIG. 2 is a diagram illustrating signals transmitted and received between the on-vehicle control device 10 and the portable machine 20 of the first embodiment, and a switching state of reception sensitivity of the on-vehicle RF reception unit 3. FIG. 3 is a flowchart illustrating operations of the on-vehicle control device 10 and the portable machine 20 of the first embodiment during keyless entry. FIG. 5 is a diagram illustrating examples of positions the on-vehicle control device 10 and the portable machine 20 and a communication state therebetween during the keyless entry.

As illustrated in FIG. 5, an arrival distance of an RF signal transmitted from the portable machine RF transmission unit 23 of the portable machine 20 is longer than an arrival distance of an LF signal transmitted from the on-vehicle LF transmission unit 2 of the on-vehicle control device 10 with respect to the vehicle 30 (this is also the same for FIGS. 6 and 7 which will be described later).

As illustrated in FIG. 2, the control unit 1 of the on-vehicle control device 10 normally sets the first reception sensitivity higher than the second reception sensitivity in the on-vehicle RF reception unit 3 (a left side of P1 in FIG. 2).

In a case where a keyless entry operation is performed in this state, first, the user performs an unlocking operation or a locking operation on the door switch 24*a* of the portable machine 20 (YES in step A1 in FIG. 3, and S1 in FIG. 2). Then, the control unit 21 causes the portable machine RF transmission unit 23 to transmit a remote control signal (RF signal) corresponding to the operation to the on-vehicle control device 10 (step A2 in FIG. 3, and S2 in FIG. 2).

In this case, as illustrated in FIG. 5, if the portable machine 20 is located within at least the arrival distance of the RF signal with respect to the vehicle 30, the remote control signal is received by the on-vehicle RF reception unit 3 of the on-vehicle control device 10 on the basis of the first reception sensitivity (YES in step A3 in FIG. 3). In other words, a signal received via the on-vehicle reception antenna 3*a* is input to the reception signal processing portion 3*c* without being attenuated in the attenuator 3*b*, and is detected as the remote control signal.

The control unit 1 collates an ID code of the portable machine 20 included in the remote control signal with the ID code of the on-vehicle control device 10. Here, if the collation between the ID codes is successful (YES in step A4 in FIG. 3), the control unit 1 controls the door lock device 13 on the basis of the remote control signal, so as to unlock or lock the door of the vehicle 30 (step A5 in FIG. 3).

On the other hand, if the collation between the ID code of the portable machine 20 included in the remote control signal and the ID code of the on-vehicle control device 10 is not successful (NO in step A4 in FIG. 3), the control unit 1 does not control the door lock device 13, and thus the door of the vehicle 30 is not locked or unlocked.

Figure 4:
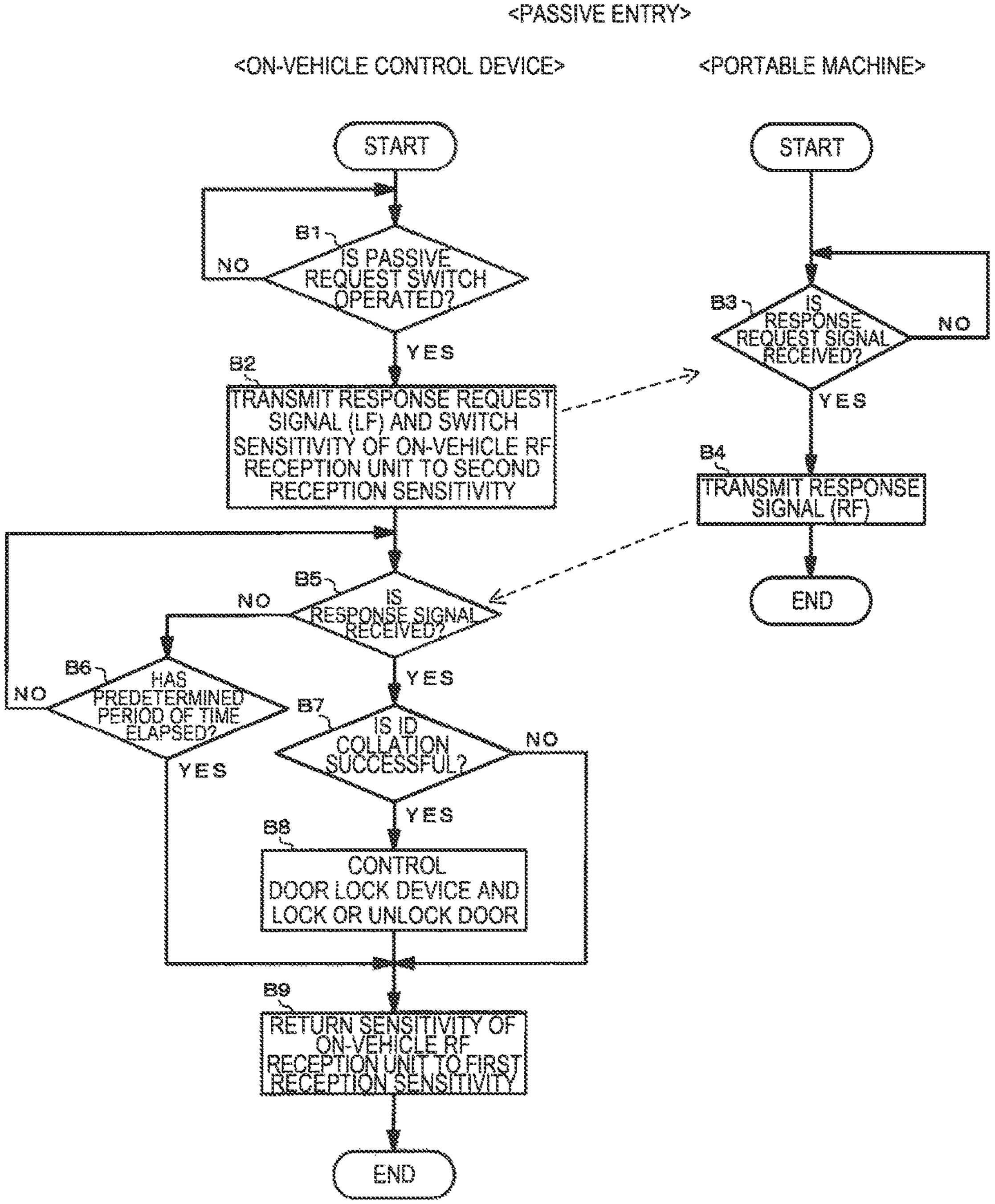
FIG. 4 is a flowchart illustrating operations of the on-vehicle control device and the portable machine illustrated in FIG. 1 during passive entry.

FIG. 4 is a flowchart illustrating operations of the on-vehicle control device 10 and the portable machine 20 of the first embodiment during passive entry. FIG. 6 is a diagram illustrating examples of positions the on-vehicle control device 10 and the portable machine 20 and a communication state therebetween during the passive entry.

During the passive entry, first, the user operates the passive request switch 11 (YES in step B1 in FIG. 4, and S3 in FIG. 2). Then, the control unit 1 of the on-vehicle control device 10 causes the on-vehicle LF transmission unit 2 to transmit a response request signal (LF signal) to the portable machine 20 (54 in FIG. 2), and switches the sensitivity of the on-vehicle RF reception unit 3 to the second reception sensitivity (P1 in FIG. 2, and step B2 in FIG. 4).

Figure 6:
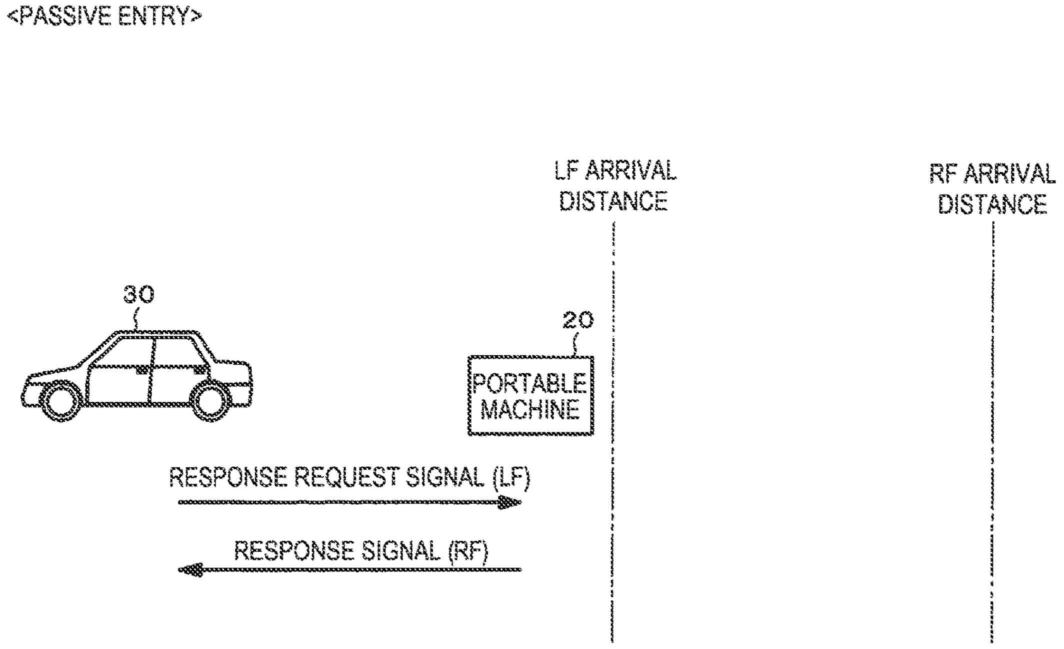
FIG. 6 is a diagram illustrating examples of positions of the on-vehicle control device and the portable machine illustrated in FIG. 1 and a communication state therebetween during passive entry.

In this case, as illustrated in FIG. 6, if the portable machine 20 is located at a position within the arrival distance of the LF signal with respect to the vehicle 30, the response request signal is received by the portable machine LF reception unit 22 (YES in step B3 in FIG. 4). Then, the control unit 21 of the portable machine 20 causes the portable machine RF transmission unit 23 to transmit a response signal including the ID code thereof to the on-vehicle control device 10 (step B4 in FIG. 4, and S5 in FIG. 2).

In the on-vehicle control device 10, the response signal is received by the on-vehicle RF reception unit 3 (YES in step B5 in FIG. 4) on the basis of the second reception sensitivity until a predetermined period of time elapses (NO in step B6 in FIG. 4) from the transmission of the response request signal (step B2 in FIG. 4). In other words, a signal received via the on-vehicle reception antenna 3*a* is attenuated in the attenuator 3*b* so as to be then input to the reception signal processing portion 3*c*, and the response signal is detected from the attenuated signal.

The control unit 1 collates an ID code of the portable machine 20 included in the response signal with the ID code of the on-vehicle control device 10. Here, if the collation between the ID codes is successful (YES in step B7 in FIG. 4), the control unit 1 controls the door lock device 13 on the basis of the response signal, so as to unlock or lock the door of the vehicle 30 (step B8 in FIG. 4). The control unit 1 returns the sensitivity of the on-vehicle RF reception unit 3 to the first reception sensitivity in order to return to a normal state (step B9 in FIG. 4, and P2 in FIG. 2).

On the other hand, in a case where a predetermined period of time has elapsed (YES in step B6 in FIG. 4) without receiving the response signal (NO in step B5 in FIG. 4) after the response request signal is transmitted (step B2 in FIG. 4), the control unit 1 returns the sensitivity of the on-vehicle RF reception unit 3 to the first reception sensitivity (step B9 in FIG. 4, and P2 in FIG. 2). In this case, the control unit 1 does not control the door lock device 13, and thus the door of the vehicle 30 is not locked or unlocked.

In a case where the collation between the ID code of the portable machine 20 included in the response signal and the ID code of the on-vehicle control device 10 is not successful (NO in step B7 in FIG. 4) even if the response signal is received (YES in step B5 in FIG. 4), the control unit 1 returns the sensitivity of the on-vehicle RF reception unit 3 to the first reception sensitivity (step B9 in FIG. 4, and P2 in FIG. 2). In this case, the control unit 1 does not control the door lock device 13, and thus the door of the vehicle 30 is not locked or unlocked.

Figure 7:
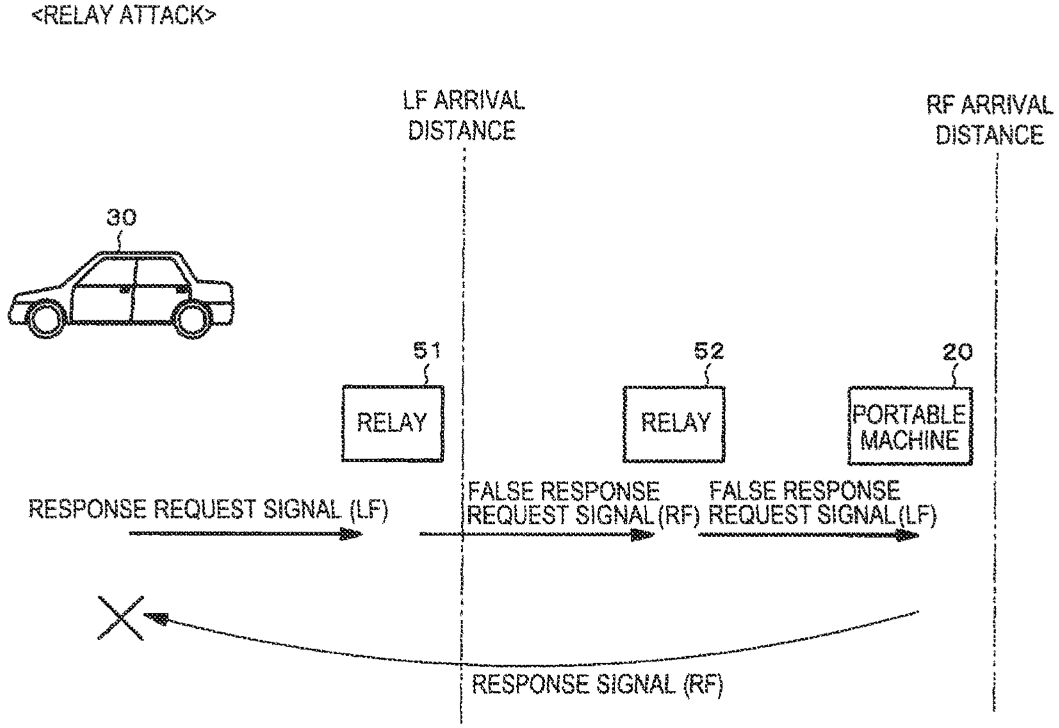
FIG. 7 is a diagram illustrating examples of positions of the on-vehicle control device and the portable machine illustrated in FIG. 1 and relays, and a communication state thereamong during a relay attack.

FIG. 7 is a diagram illustrating examples of positions of the on-vehicle control device 10, the portable machine 20, and relays 51 and 52, and a communication state thereamong during relay attack.

In the example illustrated in FIG. 7, the portable machine 20 is not located within an arrival distance of the LF signal, and is located within an arrival distance of the RF signal, with respect to the vehicle 30. One relay 51 of the relays 51 and 52 used for the relay attack is located within the arrival distance of the LF signal with respect to the vehicle 30, and the other relay 52 is located at a position where the other relay 52 can communicate with one relay 51 and the portable machine 20. The relays 51 and 52 have a function of relaying an LF signal transmitted from the on-vehicle control device 10, but do not have a function of relaying an RE signal transmitted from the portable machine 20.

As illustrated in FIG. 7, in a case where a relay attack (illegal passive entry) using the relays 51 and 52 is performed, first, a malicious third party operates the passive request switch 11 (YES in step B1 in FIG. 4, and S3 in FIG. 2). Then, the control unit 1 of the on-vehicle control device 10 causes the on-vehicle LF transmission unit 2 to transmit a response request signal (LF signal) to the portable machine 20 (S4 in FIG. 2), and switches the sensitivity of the on-vehicle RF reception unit 3 to the second reception sensitivity (P1 in FIG. 2, and step B2 in FIG. 4).

One relay 51 receives a response request signal transmitted by the on-vehicle LF transmission unit 2, and transmits a false response request signal (RF signal) imitating the signal. The other relay 52 receives the false response request signal, and further transmits the false response request signal (LF signal) to the portable machine 20. Thus, in the portable machine 20, the portable machine LF reception unit 22 receives the false response request signal (YES in step B3 in FIG. 4), and the portable machine RE transmission unit 23 transmits a response signal (RF signal) to the on-vehicle control device 10 (step B4 in FIG. 4, and S5 in FIG. 2).

However, since the portable machine 20 is not located at the position within the arrival distance of the LF signal with respect to the vehicle 30, the response signal transmitted by the portable machine RF transmission unit 23 is received via the on-vehicle reception antenna 3*a* of the on-vehicle control device 10, but the signal intensity thereof is weak. In this case, since the sensitivity of the on-vehicle RF reception unit 3 is switched to the second reception sensitivity, the signal received via the on-vehicle reception antenna 3*a* is attenuated by the attenuator 3*b*, and thus the signal intensity becomes weaker. Thus, the response signal is not detected from the attenuated signal in the reception signal processing portion 3*c*. In other words, the response signal is not received by the ort-vehicle RF reception unit 3 on the basis of the second reception sensitivity (NO in step B5 in FIG. 4). If a predetermined period of time elapses in this state (YES in step B6 in FIG. 4), the control unit 1 returns the sensitivity of the on-vehicle RF reception unit 3 to the first reception sensitivity (step B9 in FIG. 4, and P2 in FIG. 2). In this case, the control unit 1 does not control the door lock device 13, and thus the door of the vehicle 30 is not locked or unlocked. In the above-described way, the relay attack using the relays 51 and 52 are stopped.

According to the first embodiment, during the keyless entry, the on-vehicle RF reception unit 3 performs reception processing on a remote control signal transmitted from the portable machine 20 on the basis of the first reception sensitivity higher than the second reception sensitivity. Therefore, in a case where the portable machine 20 is located within an arrival distance of an RF signal even if the portable machine 20 is not located in the vicinity of the vehicle 30, the remote control signal can be reliably received by the on-vehicle control device 10, and thus the door can be locked or unlocked. During the passive entry, the on-vehicle RF reception unit 3 performs reception processing on a response signal transmitted from the portable machine 20 on the basis of the second reception sensitivity lower than the first reception sensitivity. Therefore, if the portable machine 20 is located in the vicinity of the vehicle 30, the response signal can be reliably received, and thus the door can be locked or unlocked. In a case where a relay attack using the relays 51 and 52 is performed, if the portable machine 20 is located at a position separated from the vehicle 30, the signal intensity of a response signal transmitted from the portable machine 20 is low so that the response signal is not received by the on-vehicle RF reception unit 3 on the basis of the second reception sensitivity, and thus the relay attack can be stopped. Since the on-vehicle control device 10 side only has to switch the sensitivity for receiving a signal between the first reception sensitivity and the second reception sensitivity, a circuit configuration of or signal processing in the portable machine 20 side is not complex. Therefore, it is possible to improve the crime prevention performance against a relay attack without making the portable machine 20 complex while securing a communication function between the on-vehicle control device 10 and the portable machine 20.

In the first embodiment, in a case where the sensitivity of the on-vehicle RF reception unit 3 is the first reception sensitivity, a signal received via the on-vehicle reception antenna 3*a* is input to the reception signal processing portion 3*c* without being attenuated, and thus a remote control signal transmitted from the portable machine 20 can be easily detected. In a case where the sensitivity of the on-vehicle RF reception unit 3 is the second reception sensitivity, a signal received via the on-vehicle reception antenna 3*a* is attenuated in the attenuator 3*b* so as to be then input to the reception signal processing portion 3*c*, and thus an illegal response signal transmitted from the portable machine 20 due to a relay attack can be hardly detected.

Next, a configuration of an on-vehicle apparatus control system 100 according to a second embodiment will be described with reference to FIG. 8.

Figure 8:
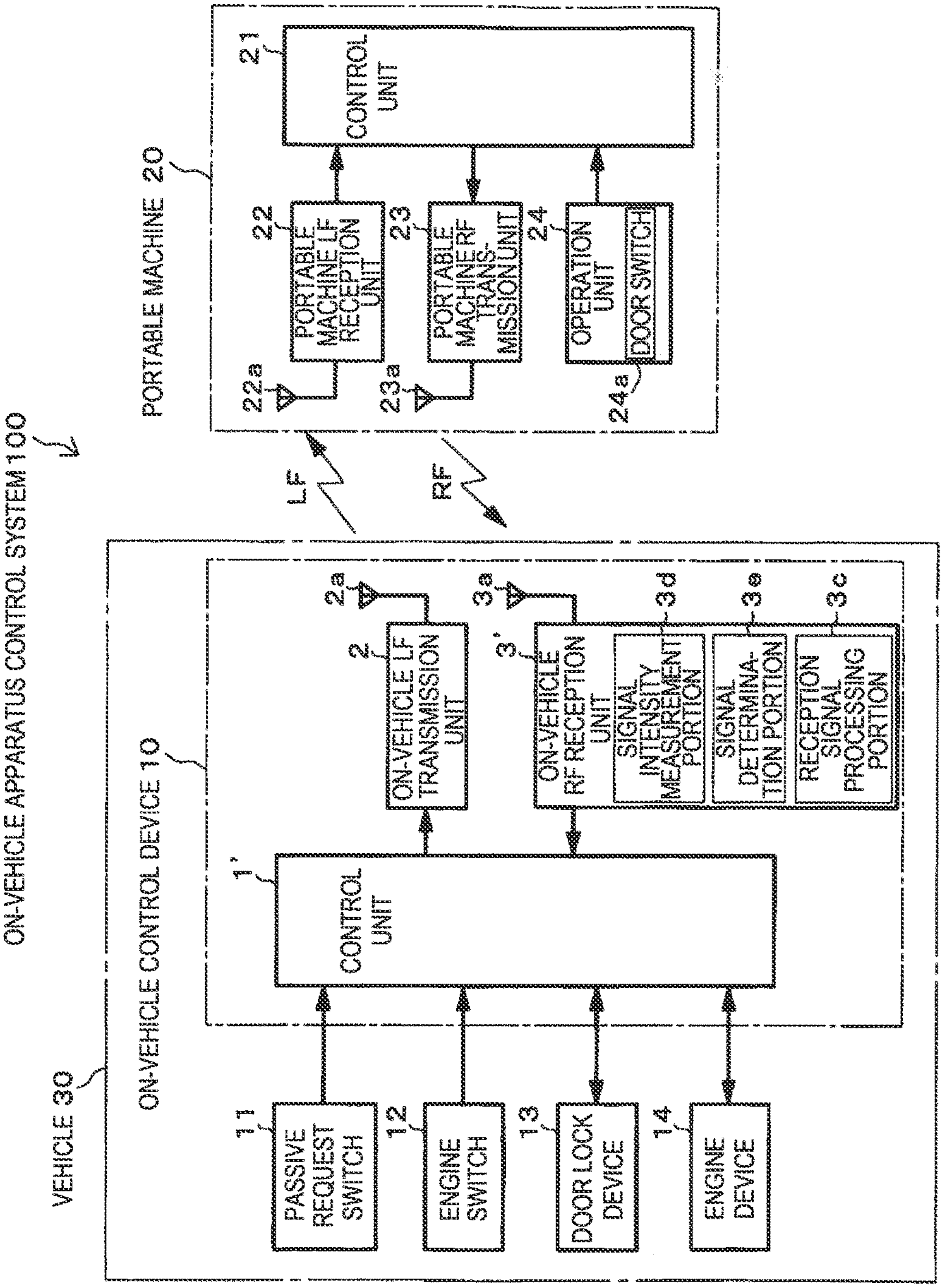
FIG. 8 is a configuration diagram of an on-vehicle apparatus control system according to a second embodiment of the present invention.

FIG. 8 is a configuration diagram of the on-vehicle apparatus control system 100 according to the second embodiment. In the second embodiment, an on-vehicle RF reception unit 3' of the on-vehicle control device 10 is constituted of an on-vehicle reception antenna 3*a*, a signal intensity measurement portion 3*d*, a signal determination portion 3*e*, a reception signal processing portion 3*c*, and the like.

The signal intensity measurement portion 3*d* measures the intensity (RSSI value) of a signal via the on-vehicle reception antenna 3*a*. The signal determination portion 3*e* determines whether or not a measured value in the signal intensity measurement portion 3*d* is equal to or greater than a predetermined threshold value. Only in a case where the measured value is equal to or greater than the predetermined threshold value, the signal determination portion 3*e* inputs the signal received via the on-vehicle reception antenna 3*a* to the reception signal processing portion 3*c*. The on-vehicle RF reception unit 3' drives the respective portions 3*a*, 3*d*, 3*e* and 3*c* so as to receive an RF signal (a remote control signal or a response signal) transmitted from the portable machine 20.

A control unit 1' of the on-vehicle control device 10 controls the on-vehicle LF transmission unit 2 and the on-vehicle RF reception unit 3' so as to perform wireless communication with the portable machine 20, and to transmit and receive signals or information to and from the portable machine 20. The control unit 1' switches a sensitivity with which the on-vehicle RF reception unit 3' receives a signal, to a first reception sensitivity or a second reception sensitivity lower than the first reception sensitivity.

Specifically, if the control unit 1' switches the sensitivity of the on-vehicle RF reception unit 3' to the first reception sensitivity, a signal received via the on-vehicle reception antenna 3*a* is input to the reception signal processing portion 3*c* without using the signal intensity measurement portion 3*d* and the signal determination portion 3*e*, and a predetermined RF signal is detected by the reception signal processing portion 3*c*. In other words, the RF signal transmitted from the portable machine 20 undergoes reception processing on the basis of the first reception sensitivity.

If the control unit 1' switches the sensitivity of the on-vehicle RF reception unit 3' to the second reception sensitivity, a signal received via the on-vehicle reception antenna 3*a* is input to the signal intensity measurement portion 3*d*, and the intensity of the signal is measured in the signal intensity measurement portion 3*d*. Only in a case where the signal determination portion 3*e* determines that a measured value is equal to or greater than a threshold value, the signal received via the on-vehicle reception antenna 3*a* is input to the reception signal processing portion 3*c*, and a predetermined RF signal is detected by the reception signal processing portion 3*c*. In other words, the RF signal transmitted from the portable machine 20 undergoes reception processing on the basis of the second reception sensitivity. In this case, if a signal received via the on-vehicle reception antenna 3*a* is a signal with low intensity, the signal is excluded by the signal determination portion 3*e* so as not to be input to the reception signal processing portion 3*c*, and thus a predetermined RF signal is not detected by the reception signal processing portion 3*c*.

Next, operations of the on-vehicle control device 10 and the portable machine 20 according to the second embodiment will be described with reference to FIGS. 3, 7 and 9.

The control unit 1' of the on-vehicle control device 10 normally sets the sensitivity of the on-vehicle RF reception unit 3' to the first reception sensitivity higher than the second reception sensitivity. Thus, during keyless entry, the on-vehicle control device 10 and the portable machine 20 are operated according to the procedures shown in FIG. 3 described above.

However, when a remote control signal is received by the on-vehicle RF reception unit 3' of the on-vehicle control device 10 on the basis of the first reception sensitivity in step A3 in FIG. 3, a signal received via the on-vehicle reception antenna 3*a* is input to the reception signal processing portion 3*c* regardless of the intensity thereof, and the remote control signal is detected.

Figure 9:
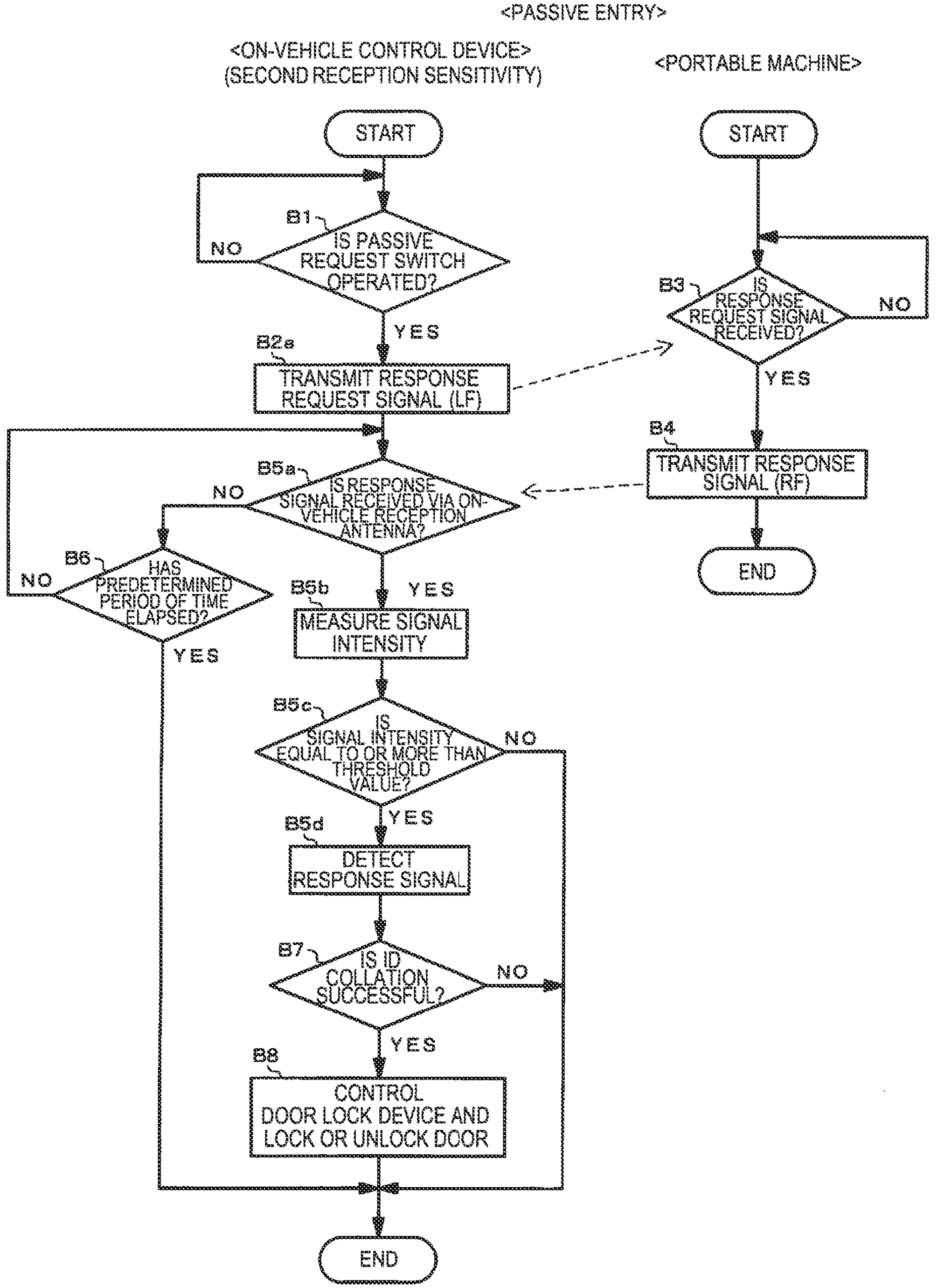
FIG. 9 is a flowchart illustrating operations of the on-vehicle control device and the portable machine illustrated in FIG. 8 during passive entry.

In contrast, during passive entry, the control unit 1' of the on-vehicle control device 10 sets the sensitivity of the on-vehicle RF reception unit 3' to the second reception sensitivity lower than the first reception sensitivity, and the on-vehicle control device 10 and the portable machine 20 are operated according to procedures shown in FIG. 9.

FIG. 9 is a flowchart illustrating operations of the on-vehicle control device 10 and the portable machine 20 of the second embodiment during the passive entry. For example, if the user operates the passive request switch 11 (YES in step B1 in FIG. 9), the control unit 1' of the on-vehicle control device 10 causes the on-vehicle LF transmission unit 2 to transmit a response request signal (LF signal) to the portable machine 20 (step B2*a* in FIG. 9).

In the portable machine 20, if the portable machine LF reception unit 22 receives the response request signal (YES in step B3 in FIG. 9), the control unit 21 causes the portable machine RF transmission unit 23 to transmit a response signal (step B4 in FIG. 9).

In the on-vehicle control device 10, if a signal is received via the on-vehicle reception antenna 3*a* (YES in step B5*b* in FIG. 9) until a predetermined period of time elapses (NO in step B6 in FIG. 9) from the transmission of the response request signal (step B2*a* in FIG. 9), the signal intensity measurement portion 3*d* measures the intensity of the signal (step B5*b* in FIG. 9). If the signal determination portion 3*e* determines that the measured value is equal to or greater than a threshold value (YES in step B5*c* in FIG. 9), the signal received via the on-vehicle reception antenna 3*a* is input to the reception signal processing portion 3*c*, and the reception signal processing portion 3*c* detects the response signal (step B5*d* in FIG. 9). In other words, the response signal is received by the on-vehicle RF reception unit 3' on the basis of the second reception sensitivity.

The control unit 1' collates an ID code of the portable machine 20 included in the response signal with an ID code of the on-vehicle control device 10. Here, if the collation between the ID codes is successful (YES in step B7 in FIG. 9), the control unit 1' controls the door lock device 13 on the basis of the response signal, so as to unlock or lock the door of the vehicle 30 (step B8 in FIG. 9).

On the other hand, as illustrated in FIG. 7, in a case where a relay attack is performed, the response signal (step B4 in FIG. 9) transmitted by the portable machine RF transmission unit 23 is received via the on-vehicle reception antenna 3*a* (YES in step B5*a* in FIG. 9), hut the signal intensity thereof is weak. Therefore, the intensity of the signal received via the on-vehicle reception antenna 3*a* is measured by the signal intensity measurement portion 3*d* (step B5*d* in FIG. 9), and then the signal determination portion 3*e* determines that the measured value is not equal to or greater than the threshold value (NO in step B5*c* in FIG. 9). In this case, the signal received via the on-vehicle reception antenna 3*a* is not input to the reception signal processing portion 3*c*, and thus the response signal is not detected from the attenuated signal in the reception signal processing portion 3*c*. Therefore, the control unit 1' does not control the door lock device 13, and thus the door of the vehicle 30 is not locked or unlocked.

Also in a case where a predetermined period of time has elapsed (YES in step B6 in FIG. 9) without receiving a signal via the on-vehicle reception antenna 3*a* (NO in step B5*a* in FIG. 9), or the collation with the ID code included in the response signal is not successful (NO in step B7 in FIG. 9), the control unit 1' does not control the door lock device 13, and thus the door of the vehicle 30 is not locked or unlocked.

According to the second embodiment, during the keyless entry, the on-vehicle RF reception unit 3' performs reception processing on a remote control signal on the basis of the first reception sensitivity, and can thus reliably receive the remote control signal so as to lock or unlock the door. During the passive entry, since the on-vehicle RF reception unit 3' performs reception processing on a response signal on the basis of the second reception sensitivity, a response signal with low signal intensity due to a relay attack is not received by the on-vehicle RF reception unit 3', and thus it is possible to stop the relay attack. A response signal with high signal intensity, transmitted from the portable machine 20 in the vicinity of the vehicle 30 can be reliably received, and thus the door can be locked or unlocked. Since the on-vehicle control device 10 side only has to switch the sensitivity for receiving a signal between the first reception sensitivity and the second reception sensitivity, a circuit configuration of or signal processing in the portable machine 20 side is not complex. Therefore, it is possible to improve the crime prevention performance against a relay attack without making the portable machine 20 complex while securing a communication function between the on-vehicle control device 10 and the portable machine 20.

In the second embodiment, in a case where the sensitivity of the on-vehicle RF reception unit 3' is the first reception sensitivity, a signal received via the on-vehicle reception antenna 3*a* is input to the reception signal processing portion 3*c* regardless of the signal intensity thereof, and thus a remote control signal transmitted from the portable machine 20 can be easily detected. In a case where the sensitivity of the on-vehicle RF reception unit 3' is the second reception sensitivity, the intensity of a signal received via the on-vehicle reception antenna 3*a* is measured, and, only in a case where the measured value is equal to or greater than a threshold value, the signal received via the on-vehicle reception antenna 3*a* is input to the reception signal processing portion 3*c*. Thus, an illegal response signal with low signal intensity transmitted from the distant portable machine 20 due to a relay attack can be hardly detected.

The present invention may employ various embodiments other than the above-described embodiments. For example, in the above-described embodiments, as illustrated in FIGS. 4 and 9, an example has been described in which, during passive entry, the sensitivity of the on-vehicle RF reception units 3 and 3' is switched to the second reception sensitivity, and reception processing is performed on a response signal transmitted from the portable machine 20 on the basis of the second reception sensitivity, but the present invention is not limited thereto. For example, as in a third embodiment shown in FIG. 10 or a fourth embodiment shown in FIG. 11, also in the polling method, in a case where a response request signal is transmitted from the on-vehicle control device 10, and the door is locked or unlocked, the sensitivity of the on-vehicle RF reception units 3 and 3' may be switched to the second reception sensitivity, and reception processing may be performed on a response signal transmitted from the portable machine 20 on the basis of the second reception sensitivity.

Figure 10:
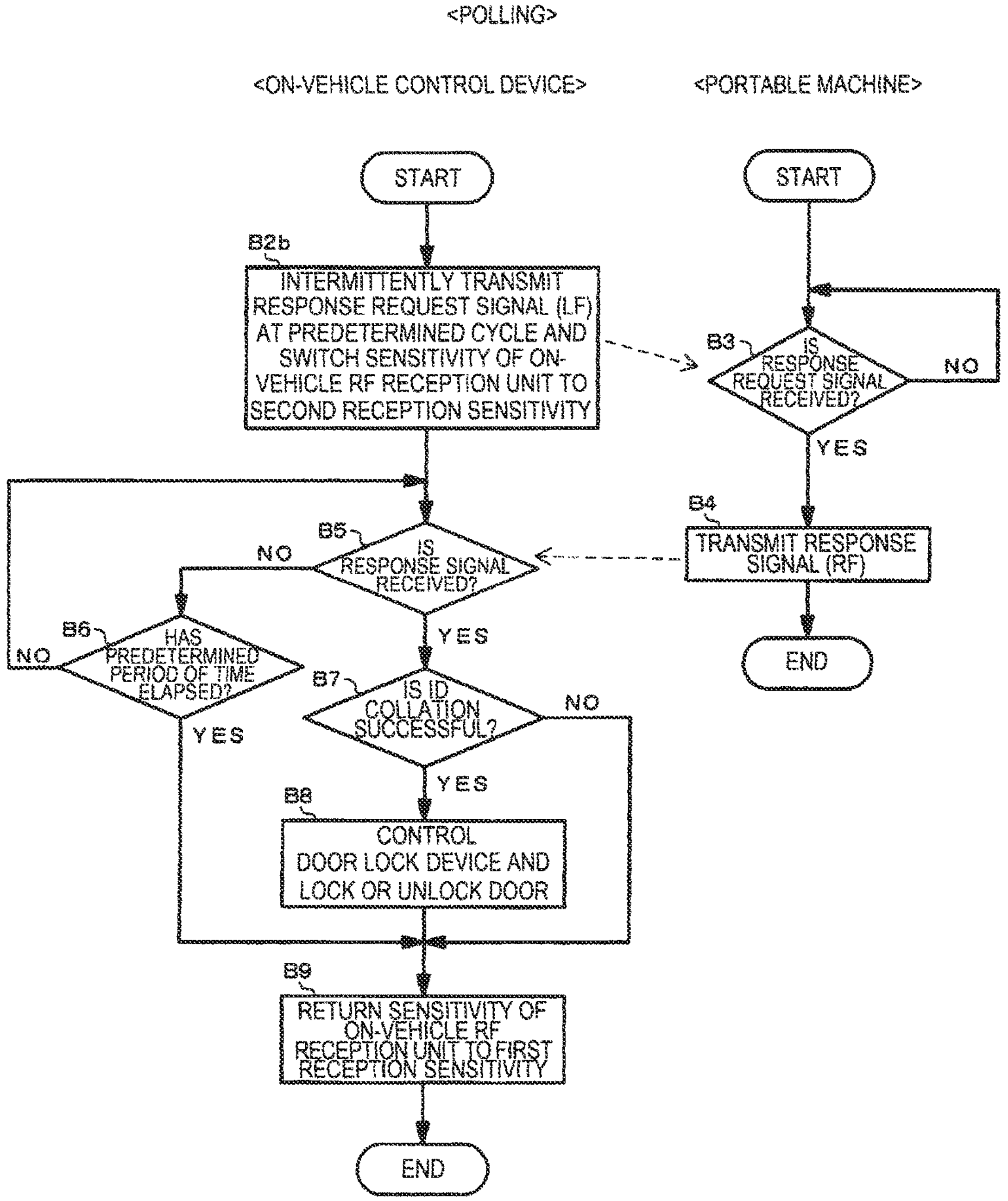
FIG. 10 is a flowchart illustrating operations of an on-vehicle control device and a portable machine according to a third embodiment of the present invention during polling.

In an example illustrated in FIG. 10, in the on-vehicle control device 10 illustrated in FIG. 1, first, a response request signal (LF signal) is intermittently transmitted from the on-vehicle LF transmission unit 2 at a predetermined cycle, and the sensitivity of the on-vehicle RF reception unit 3 is switched to the second reception sensitivity (step B2*b* in FIG. 10). The subsequent procedures are the same as the procedures described in FIG. 4.

Figure 11:
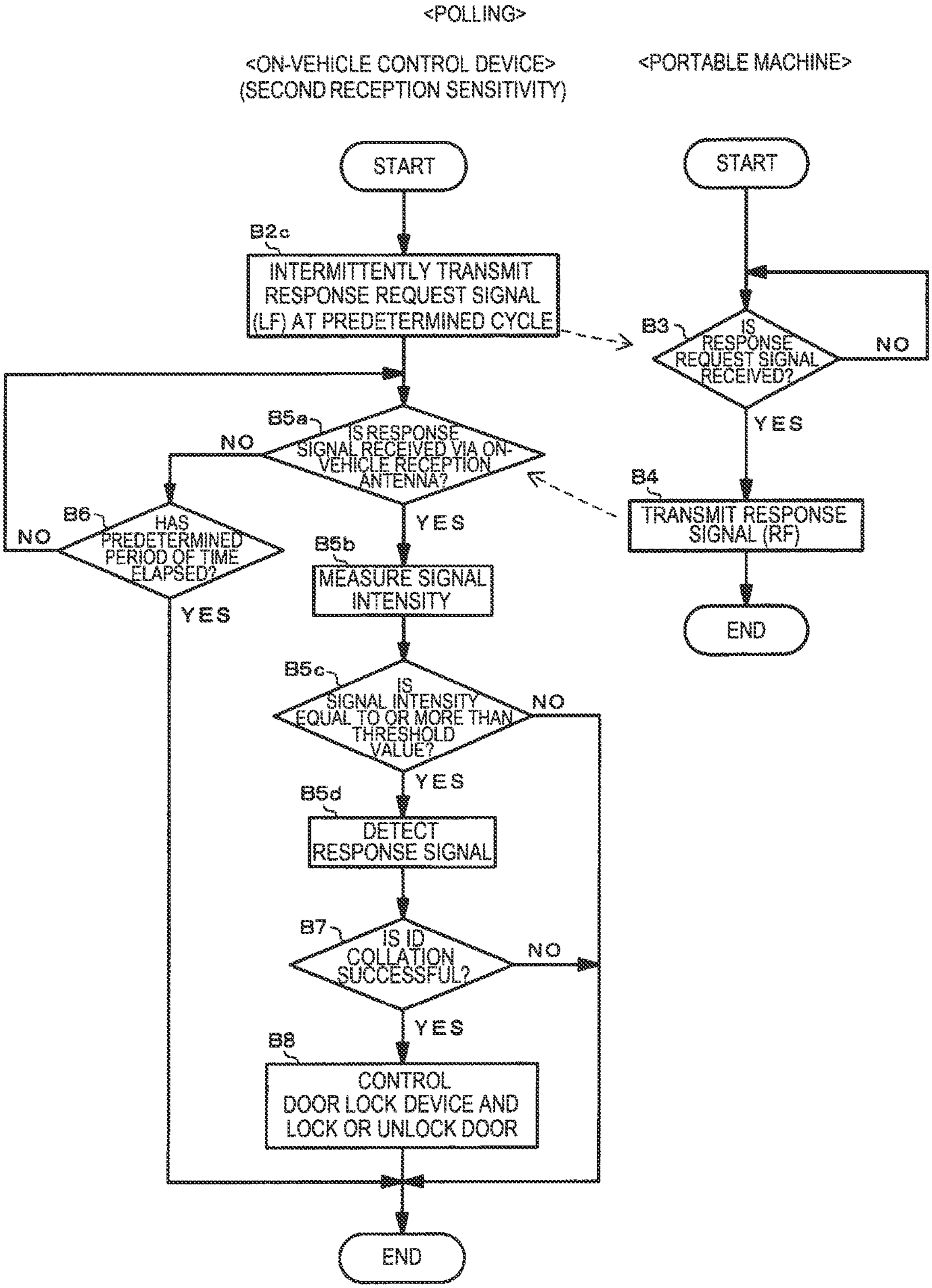
FIG. 11 is a flowchart illustrating operations of an on-vehicle control device and a portable machine according to a fourth embodiment of the present invention during polling.

In an example illustrated in FIG. 11, in the on-vehicle control device 10 illustrated in FIG. 8, first, a response request signal is intermittently transmitted from the on-vehicle LF transmission unit 2 at a predetermined cycle (step B2*c* ifs FIG. 11). The subsequent procedures are the same as the procedures described in FIG. 9.

According to the third embodiment and the fourth embodiment, also in a case where the door is locked or unlocked in the polling method, since the on-vehicle RF reception units 3 and 3' perform reception processing on a response signal on the basis of the second reception sensitivity, a response signal with low signal intensity due to a relay attack is not received by the on-vehicle RF reception units 3 and 3', and thus the relay attack can be stopped.

In the embodiment shown in FIG. 4 or 10, an example has been described in which a response request signal is transmitted, the sensitivity of the on-vehicle RF reception unit 3 or 3' is switched to the second reception sensitivity, and the sensitivity of the on-vehicle RF reception unit 3 or 3' is returned to the first reception sensitivity after a response signal is received and then the door is locked or unlocked, or after a predetermined period of time elapses without receiving the response signal, but the present invention is not limited thereto. For example, the sensitivity of the on-vehicle RF reception unit 3 or 3' may be switched to the second reception sensitivity right before or right after a response request signal is transmitted. For example, the sensitivity of the on-vehicle RF reception unit 3 or 3' may be returned to the first reception sensitivity right after a response signal is received, or after a predetermined period of time elapses without receiving a response signal. In other words, in a case where a response signal transmitted from the portable machine 20 in response to a response request signal is received, the sensitivity of the on-vehicle RF reception unit 3 or 3' may be set to the second reception sensitivity.

In the above-described embodiments, as an example of control on an on-vehicle apparatus performed by the on-vehicle apparatus control system 100, locking or unlocking of the door performed by the door lock device 13 has been described, but the present invention is not limited thereto. For example, control on other on-vehicle apparatuses such as starting of the engine performed by the engine device 14 mounted on the vehicle, driving of an air conditioner performed by an air conditioner device, and driving of an audio system may be performed.

In the above-described embodiments, a description has been made of an example in which the present invention is applied to the on-vehicle apparatus control system 100 and the on-vehicle control device 10 for an automatic four-wheel vehicle, but the present invention is also applicable to an on-vehicle apparatus control system and an on-vehicle control device for other vehicles such as a motorcycle or a large vehicle.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

The invention claimed is:

1. An on-vehicle apparatus control system comprising:
an on-vehicle control device mounted on a vehicle; and
a portable machine carried by a user,
wherein the on-vehicle control device comprises:
an on-vehicle transmitter that transmits a response request signal to the portable machine; and
an on-vehicle receiver that receives a response signal and a remote control signal from the portable machine,
wherein the portable machine comprises:
a portable machine receiver that receives the response request signal from the on-vehicle control device;
an operation switch with which an on-vehicle apparatus mounted on the vehicle is operated; and
a portable machine transmitter that transmits the response signal in response to reception of the response request signal, and transmits the remote control signal in response to an operation on the operation switch,
wherein the on-vehicle control device controls the on-vehicle apparatus based on the response signal or the remote control signal received by the on-vehicle apparatus receiver, and
wherein the on-vehicle receiver performs:
reception processing on the remote control signal based on a first reception sensitivity when receiving the remote control signal transmitted from the portable machine transmitter, and the remote control signal undergoes the reception processing without being attenuated; and
reception processing on the response signal based on a second reception sensitivity lower than the first reception sensitivity when receiving the response signal transmitted from the portable machine transmitter, and the response signal undergoes the reception processing after being attenuated.

2. The on-vehicle apparatus control system according to claim 1,
wherein the on-vehicle transmitter transmits the response request signal when an on-vehicle switch disposed in the vehicle is operated, or intermittently at a predetermined cycle.

3. The on-vehicle apparatus control system according to claim 1,
wherein the on-vehicle receiver comprises:
an on-vehicle reception antenna via which an external signal is received; and
an attenuator that attenuates a signal received via the on-vehicle reception antenna, and
wherein the on-vehicle receiver performs:
in the first reception sensitivity, a process of detecting the remote control signal from a signal received via the on-vehicle reception antenna; and
in the second reception sensitivity, a process of attenuating a signal received via the on-vehicle reception antenna with the attenuator, and detecting the response signal from an attenuated signal.

4. The on-vehicle apparatus control system according to claim 1,
wherein the on-vehicle receiver comprises:
an on-vehicle reception antenna via which an external signal is received; and
a signal intensity measurement portion that measures the intensity of a signal received via the on-vehicle reception antenna, and
wherein the on-vehicle receiver performs:
in the first reception sensitivity, a process of detecting the remote control signal from a signal received via the on-vehicle reception antenna; and
in the second reception sensitivity, a process of measuring the intensity of a signal received via the on-vehicle reception antenna with the signal intensity measurement portion, and detecting the response signal from the signal received via the on-vehicle reception antenna only in a case where a measured value is equal to or greater than a threshold value.

5. An on-vehicle control device mounted on a vehicle, said on-vehicle control device comprising:

an on-vehicle transmitter that transmits a response request signal to a portable machine carried by a user; and an on-vehicle receiver that receives a response signal transmitted from the portable machine in response to reception of the response request signal, and a remote control signal transmitted from the portable machine in response to an operation on an operation switch disposed in the portable machine, wherein said on-vehicle control device controls an on-vehicle apparatus based on the response signal or the remote control signal received by the on-vehicle receiver, and wherein the on-vehicle receiver performs:

reception processing on the remote control signal based on a first reception sensitivity when receiving the remote control signal transmitted from the portable machine and the remote control signal undergoes the reception processing without being attenuated; and reception processing on the response signal based on a second reception sensitivity lower than the first reception sensitivity when receiving the response signal transmitted from the portable machine, and the response signal undergoes reception processing after being attenuated.

6. The on-vehicle control device according to claim 5, wherein the on-vehicle transmitter transmits the response request signal when an on-vehicle switch disposed in the vehicle is operated, or intermittently at a predetermined cycle.

7. The on-vehicle control device according to claim 5, wherein the on-vehicle receiver comprises:

an on-vehicle reception antenna via which an external signal is received; and an attenuator that attenuates a signal received via the on-vehicle reception antenna, and wherein the on-vehicle receiver performs:

in the first reception sensitivity, a process of detecting the remote control signal from a signal received via the on-vehicle reception antenna; and in the second reception sensitivity, a process of attenuating a signal received via the on-vehicle reception antenna with the attenuator, and detecting the response signal from an attenuated signal.

8. The on-vehicle control device according to claim 5, wherein the on-vehicle receiver comprises:

an on-vehicle reception antenna via which an external signal is received, and a signal intensity measurement portion that measures the intensity of a signal received via the on-vehicle reception antenna, and wherein the on-vehicle receiver performs:

in the first reception sensitivity, a process of detecting the remote control signal from a signal received via the on-vehicle reception antenna; and in the second reception sensitivity, a process of measuring the intensity of a signal received via the on-vehicle reception antenna with the signal intensity measurement portion, and detecting the response signal from the signal received via the on-vehicle reception antenna only in a case where a measured value is equal to or greater than a threshold value.

* * * * *